United States Patent
Escher et al.

(10) Patent No.: US 9,435,778 B2
(45) Date of Patent: Sep. 6, 2016

(54) METHODS AND SYSTEMS FOR EXPERIMENTAL SET-UP AND DATA ANALYSIS IN TARGETED PROTEOMICS APPLICATIONS

(71) Applicant: BiognoSYS AG, Schlieren (CH)

(72) Inventors: Claudia Escher, Riehen (CH); Reto Ossola, Dagmersellen (CH); Oliver Rinner, Zurich (CH); Lukas Reiter, Thalwil (CH)

(73) Assignee: BiognoSYS AG, Schlieren (CH)

( * ) Notice: Subject to any disclaimer, the term of this patent is extended or adjusted under 35 U.S.C. 154(b) by 208 days.

(21) Appl. No.: 14/347,715

(22) PCT Filed: Sep. 20, 2012

(86) PCT No.: PCT/CH2012/000217
§ 371 (c)(1),
(2) Date: Mar. 27, 2014

(87) PCT Pub. No.: WO2013/044401
PCT Pub. Date: Apr. 4, 2013

(65) Prior Publication Data
US 2014/0236497 A1      Aug. 21, 2014

(30) Foreign Application Priority Data
Sep. 28, 2011  (CH) .................................. 1595/11

(51) Int. Cl.
*G01N 30/86*  (2006.01)
*G01N 30/88*  (2006.01)
G01N 30/04   (2006.01)

(52) U.S. Cl.
CPC ...... *G01N 30/8675* (2013.01); *G01N 30/8672* (2013.01); *G01N 30/88* (2013.01); G01N 2030/042 (2013.01); G01N 2030/8831 (2013.01)

(58) Field of Classification Search
USPC .......................................................... 702/30
See application file for complete search history.

(56) References Cited

U.S. PATENT DOCUMENTS

2009/0317791 A1    12/2009 Gorenstein et al.

FOREIGN PATENT DOCUMENTS

| WO | 2007/012643 A1 | 2/2007 |
| WO | 2010/060218 A1 | 6/2010 |
| WO | 2012/035412 A2 | 3/2012 |

OTHER PUBLICATIONS

Kosaku Shinoda, Aligning LC peaks by converting gradient retention times to retention index of peptides in proteomic experiments, Advance Access publication May 19, 2008, vol. 24 No. 14 2008, pp. 1590-1595.*

(Continued)

*Primary Examiner* — Tung Lau
(74) *Attorney, Agent, or Firm* — Sughrue Mion, PLLC

(57) ABSTRACT

A method of the analysis of compounds with mass spectrometry and to instruments, substances, and methods for polypeptide analysis, in particular in targeted proteomics applications and based on indexed retention times as peptide specific property. The method of chemical analysis comprises the steps of: a) providing a first sample comprising peptides; b) performing LC-MS and determining the empirical retention time values of the peptides; c) translating the empirical retention time values into the indexed retention time scale and associating a reference indexed retention time value; d) providing a second complex sample comprising peptides; e) performing LC-MS and determining the empirical retention time values; f) translating the empirical retention time values of the peptides into the indexed retention time scale by numerically adapting the transformation function; and g) determining the predicted empirical retention time value of the peptides by using the numerically adapted transformation function determined in step f).

22 Claims, 9 Drawing Sheets

(56) References Cited

OTHER PUBLICATIONS

Damon May, Received Jun. 18, 2008, Peptide Sequence Confidence in Accurate Mass and Time Analysis and Its Use in Complex Proteomics Experiments, p. 5148-5156.*
Valeri I. Babushok, Retention Characteristics of Peptides in RP-LC: Peptide Retention Prediction, Online publication: Aug. 26, 2010, p. 781-797.*
Valeri I. Babushok et al., "Retention Characteristics of Peptides in RP-LC: Peptide Retention Prediction", Chromatographia, Nov. 2010, p. 781-797, vol. 72, No. 9.
Lukas Reiter et al., "mProphet: automated data processing and statistical validation for large-scale SRM experiments", Nature Methods, May 2011, 9 pgs., vol. 8, No. 5.
J.M.R. Parker et al., "New Hydrophilicity Scale Derived from High-Performance Liquid Chromatography Peptide Retention Data: Correlation of Predicted Surface Residues with Antigenicity and X-ray-Derived Accessible Sites", Biochemistry 1986, pp. 5425-5432, vol. 25.
International Search Report for PCT/CH2012/000217 dated Jan. 7, 2013.

* cited by examiner

METHODS AND SYSTEMS FOR EXPERIMENTAL SET-UP AND DATA ANALYSIS IN TARGETED PROTEOMICS APPLICATIONS

CROSS REFERENCE TO RELATED APPLICATIONS

This application is a National Stage of International Application No. PCT/CH2012/000217 filed Sep. 20, 2012, claiming priority based on Swiss Patent Application No. 1595/11 filed Sep. 28, 2011, the contents of all of which are incorporated herein by reference in their entirety.

TECHNICAL FIELD

The present invention relates to the analysis of compounds with mass spectrometry and more particularly to substances and methods for polypeptide analysis, in particular in targeted proteomics applications and based on indexed retention-time as peptide specific property.

PRIOR ART

Liquid chromatography coupled to Mass Spectrometry (LC-MS) has now been used for many years in the proteomic community for the identification and quantification of peptides (and thus proteins) from complex sample mixtures. In proteomics, the analytes are typically peptides generated by tryptic digestion of protein samples. The commonly most used approaches are variants of the so called LC-MS/MS or "shotgun" MS approach that is based on the generation of fragment ions from precursor ions that are automatically selected based on the precursor ion profiles (data dependent analysis, DDA). A main shortcoming of these methods is poor reproducibility which results in only partially overlapping protein sets in repeated analysis of substantially similar samples. Several new approaches have recently been developed that address these limitations and which can conceptually be described as targeted proteomics approaches.

The most mature technology is called selected Reaction Monitoring (SRM), frequently also referred to as multiple reaction monitoring (MRM). The targets for MRM experiments are defined on a rational basis and depend on the hypothesis to be tested in the experiment. Selected combinations of precursor ions and fragment ions (so called transitions, the set of transitions for one target precursor is called MRM assays) for these targets are programmed into a mass spectrometer, which then generates measurement data only for the defined targets.

Another variant of targeted proteomics is data independent acquisition, and a more recently presented variant commonly called SWATH-MS approach. Here, the targeted aspect is introduced only on the data analysis level. Contrary to MRM, this approach does not require any preliminary method design prior to the sample injection. Since the LC-MS acquisition covers the complete analyte contents of a sample through the entire mass and retention time (RT) ranges the data can be mined a posteriori for any peptide/precursor of interest. Data is acquired in a data independent manner, on the complete mass range (e.g. 200-2000 Thomson) and through the entire chromatography, disregarding of the content of the sample. This is commonly achieved by stepping the selection window of the mass analyzer step by step through the complete mass range. In effect, this data acquisition method generates a complete fragment ion map for all the analytes present in the sample and relates the fragment ion spectra back to the precursor ion selection window in which the fragment ion spectra were acquired. This is achieved by widening the precursor isolation windows on the mass analyzer and thus accounting a priori for multiple precursors co-eluting and concomitantly participating to the fragmentation pattern recorded during the analysis. Such a precursor window is called a swath. The result is complex fragment ion spectra from multiple precursor fragmentations, that require a more challenging data analysis.

Unlike in shotgun proteomics, for the MRM and SWATH technology spectra are repeatedly recorded for the same analytes with a high time resolution. The high time resolution when compared to shotgun proteomics, together with the limited fragment ion information for MRM and the limited fragment ion to precursor ion association for SWATH, makes a completely new type of data analysis necessary. Since only a limited number of pre-defined analytes are being monitored, it is not necessary to make a shotgun proteomics type database search by comparing the spectra to a complete theoretical proteome. Instead, a number of scores have been described that are based on signal features such as shape, co-elution of transitions, and similarity of transition intensities to assay libraries.

Furthermore, confidence estimation of identification in MRM by means of false discovery rates cannot be done as for the classical shotgun proteomics. Therefore, a novel approach has been developed by measuring transitions for non-existing peptides (decoy transitions) (Reiter L, Rinner O, Picotti P, Huttenhain R, Beck M, Brusniak M Y, Hengartner M O, Aebersold R: mProphet: automated data processing and statistical validation for large-scale SRM experiments. Nature methods 2011, 8(5):430-435). The data from these decoy transitions can be used to derive false discovery rates as is done in shotgun proteomics. This confidence estimation by means of false discovery rate is necessary to determine the data significance level and allow user defined quality filtering of the data.

SWATH data are distinct from MRM data. In contrast to MRM, full fragment ion spectra are recorded using the SWATH method. The time resolution is usually chosen similarly as in MRM. When comparing SWATH with shotgun proteomics, the difference is that in SWATH the fragment ion spectra are derived from a much higher number of precursors because the window for precursor selection is usually chosen as high as 25Th instead of roughly 1Th for shotgun proteomics (reference is made in this respect to the priority applications EP 10 009595.9 and U.S. 61/383,137 and the corresponding subsequent published applications claiming priority thereof). This high complexity of the fragment ion spectra makes it unpractical to analyze the data as in shotgun proteomics using database searches. However, the data can be analyzed similarly to MRM data with the additional benefit of the high time resolution in the data. This can be done by extracting ion currents corresponding to transitions in MRM. The resulting data can then be analyzed very similarly to MRM.

In all variants of LC coupled mass spectrometry, proteins in samples for MRM experiments are digested into smaller peptides prior to the analysis. The resulting peptide mixture is usually chromatographically separated in order to reduce the complexity of the sample. Chromatographic separation adds a time dimension to the recorded data of the mass spectrometer, the retention time (RT).

The differences in the RT of peptides for a specific LC-setup, the RT variance, are composed of essentially three main factors: (i) peptide-intrinsic properties, (ii) variance in the LC-system, and (iii) residual variance.

Peptide intrinsic retention (i) is specific for each peptide (sequence, potentially modified) and determined by its physicochemical properties in particular in the context of chromatography specific parameters (mobile phase composition, pH of mobile phase for LC, stationary phase), in a way that defies highly accurate prediction.

The setup of the chromatographic system (e.g. solvent gradient, and/or column material, and/or dead volumes in the LC system) can affect all peptides in a consistent way and is called here LC-variance (ii).

The residual variance (iii) is composed of variability in the LC-system, such as effects of varying sample concentrations (resulting in overloading) or variations in pump pressure, temperature etc.

In shotgun proteomics, usually, RT variations do not influence the data analysis process since the RT is only used within one LC-MS/MS run to put the spectra into chronological order. US2009/0317791 on the other hand discloses that RT can be used to improve peptide identification.

For targeted proteomics in contrast, prediction of accurate peptide RTs can significantly improve the performance and scale of the experiments by allowing acquisition to be scheduled. Transitions can be measured for only a small window of time around when the peptide is expected to elute from the chromatographic column, the RT. This scheduling increases the number of transitions that can be measured in one LC-MRM run, since at any given time, the instrument measures only a subset of the transitions in the method. The duration of the measurement window used for scheduling is usually chosen based on the anticipated accuracy of the predicted peptide RTs. Generally, more accurate predicted RTs allow RT windows of shorter duration.

Due to the inherent RT variance described above however, the window must always be significantly wider than the actual peak width (retention time range where an analyte elutes from the chromatographic system). In general, the shorter the duration of measurement for each peptide, the more peptides may be measured in a single run.

Valeri et al. discuss in their review the peptide retention times and their usage. The review focuses on the concept of using retention times for the discovery of novel peptides. The empirical measurement of all peptides in a complete theoretical proteome (let alone potential peptide modifications and combinations thereof and peptide truncations) is not practical because the number of tryptic peptides in such a complete theoretical proteome is extremely large (e.g. >10^6). Therefore, the review focuses on in silico prediction of retention times. In silico prediction is mainly based on physicochemical coefficients of amino acids determined beforehand (without empirical measurement of the complete theoretical proteome). In the context of in silico prediction Valeri et al. also discuss the concept of indexed retention time for calibration of in silico predicted retention times (S. 782, eq (4)). In silico prediction has the advantage that retention times for complete theoretical proteomes can be determined. The disadvantage is that these predicted retention times are significantly less accurate than the ones empirically determined. Further, handling all possible chemical peptide modifications with in silico prediction is in practice extremely difficult. SSRCalc, an algorithm for in silico prediction, for example, does not support prediction for modified peptides.

In WO 2010/060218 A1 a specific method, SSRCalc, for the above mentioned prediction of retention times is described. Further, a set of peptides is described that is used to calibrate the method for retention time prediction. SSRCalc relies on previous experiments (e.g. Guo et al., Journal of Chromatography 359 (1986), 499-517). Empirically determined retention coefficients are used during model development of SSRCalc and related to experimentally determined retention times. A number of additional parameters such as the position of the amino acid relative to the N-terminus and sequence length are also used. The resulting SSRCalc algorithm can use this model to predict relative retention values for any amino acid sequence for which no previously measured retention time has been recorded.

SUMMARY OF THE INVENTION

It is therefore an object of the present invention to provide an improved method for chemical analysis of polypeptide mixtures, in particular for the application in the proteomics field involving the spectroscopic analysis of complex mixtures of polypeptides and/or proteins. The polypeptides and/or proteins include biological derivatives thereof such as phosphorylated polypeptides and/or proteins, glycosylated polypeptides and/or proteins, acetylated polypeptides and/or proteins, methylated polypeptides and/or proteins or oxidized polypeptides and/or proteins and combinations thereof. The polypeptides and/or proteins include naturally occurring as well as synthetically derived forms containing various variants of isotopes such as carbon $^{13}$C), hydrogen ($^{1}$H, $^{2}$H), nitrogen ($^{14}$N, $^{15}$N), oxygen ($^{16}$O, $^{17}$O, $^{18}$O) and sulfur ($^{32}$S, $^{33}$S, $^{34}$S, $^{36}$S) and combinations thereof.

Some embodiments of the invention arise from the realization that the retention time (RT) is a peptide intrinsic and specific property that can in principle serve to set up targeted proteomics experiments (e.g. for scheduled MRM) and to analyze LC-MS data (e.g. SWATH). The practical use of RT, however, has so far been limited by the lack of accuracy of in silico algorithms, variance introduced by variability of chromatographic systems and lack of reproducibility of setup of the same.

The invention describes methods to normalize RT based on determination of the RT in relation to a defined set of reference peptides. This indexed retention time (iRT) is a stable dimensionless value for each peptide.

The invention describes further the application of iRT in various types of the analysis of data from LC-MS experiments. Specifically, by measuring a sample together with a set of reference peptides an empirical iRT value, adapted numerically each time when an experiment is carried out, can be derived that can improve scoring of MRM and SWATH data. Furthermore, the invention describes how slices of data can be extracted from LC-MRM and LC-SWATH data based on the iRT concept to improve data analysis. As concerns the LC-SWATH technology reference is made to EP 10 009595.9 and U.S. 61/383,137 and the corresponding subsequent published applications claiming priority thereof. The disclosure of these referenced applications is to be included into the specification as concerns the LC-SWATH technology.

Several aspects of the invention also apply to any other data recording method (similar to SWATH), where fragment ion spectra are recorded with a high time resolution such that a typical peak resulting from the elution of an analyte is reasonably well characterized in terms of peak start, apex and end. This is the case for instance if on average more than two data points are recorded for a peak. Such a method can partition the precursor m/z range and/or fragment m/z range into one or many of segments (similar to SWATH). These methods can also be scheduled acquisition methods (similar to MRM) or non-scheduled acquisition methods (similar to SWATH).

More specifically, the proposed method is a method of chemical analysis, comprising at least the following steps:
a) providing a first complex sample comprising a set of at least two reference peptides associated to an indexed retention time scale (iRT), as well as at least one further peptide,
b) performing LC-MS on said complex sample and determining the empirical retention time values (RTe) of the reference peptides and of the at least one further peptide,
c) translating the empirical retention time values (RTe) of the reference peptides and of the at least one further peptide into the indexed retention time scale and associating to each reference peptide a reference indexed retention time value (iRTr) and to the at least one further peptide an associated indexed retention time value (iRTa),
d) providing a second complex sample comprising at least one polypeptide as well as said set of the at least two reference peptides,
e) performing LC-MS on said second complex sample and determining the empirical retention time values (RTe) of the reference peptides,
f) translating the empirical retention time values (RTe) of the reference peptides into the indexed retention time scale by numerically adapting the transformation function for the conversion of the retention time values (RTe) into indexed retention time values such that the calculated indexed retention time values (iRTe), calculated based on the measured retention time values (RTe) of the reference peptides, optimally match the assigned indexed retention time values (iRTr) of the reference peptides,
g) determining the predicted empirical retention time value (RTp) of the at least one further peptide by using the numerically adapted transformation function determined in step f).

As one can see from the above, it is one of the gists of the present invention, in the first step, to set up an indexed retention time scale iRT based on a set of reference peptides. Each reference peptide is given a defined value in this indexed retention time scale.

In contrast to the known and above discussed SSRCalc or in general in silico retention time prediction, as proposed herein "gold standard" iRTa values are determined empirically in c) and analytical iRTe are determined empirically in f).

In the above method LC-MS can also be replaced by LC-UV technologies or other LC-XX technologies, as long as one, normally the first, "dimension" is an LC step.

It should be noted that the concept can equivalently be applied not only to target peptides and correspondingly using reference peptides, but can also be applied for example to target small organic molecules, target lipids, target carbohydrates, target DNA fragments, target RNA fragments, and their derivatives or the like, where then correspondingly normally reference small organic molecules, reference lipids, target carbohydrates, reference DNA fragments, reference RNA fragments, respectively, are used.

As concerns steps a)-c), normally (but not necessarily) first, the iRTr of the reference peptides are determined (using formula (1) below) in an LC-MRM run with only the retention time peptides for the definition of iRTr values, and second, the target peptides are measured together with the retention time peptides and the iRTa is determined.

At the same time or in a subsequent step one or a multitude of target peptides is analyzed together with the reference peptides in essentially the same or a similar experiment, and also these target peptides are attributed corresponding values in the indexed retention time scale. If in a preceding step this indexed retention time scale has been established for the reference peptides, this attribution is carried out by first using the empirically measured retention times of the reference peptides, and by using a numerical optimization, typically a linear regression (however, also other functions like polynomial functions or a set of functions e.g. linear functions in between neighbouring reference peptides are possible), adapting the function for the back calculation of the values of the reference peptide retention times from the empirically measured values to the values in the indexed retention time scale. Using the corresponding parameters of this function that is determined for the reference peptides, the corresponding associated indexed retention time value is calculated from the empirically measured retention time of the target peptides. Like this it is made sure that the indexed retention time value for the target peptides is as much as possible independent from the experimental conditions.

For the actual analytical runs this so to speak normalized indexed retention time scale based on the reference peptides as well as the specific values in this indexed retention time scale of the target peptides are used. This is done specifically by, for each analytical run, first determining the empirical retention times of the reference peptides of the corresponding analytical run. If some of these reference peptide peaks are not accessible, for example due to masking or the like, they can also be left out. Again, using these empirically measured retention times of the reference peptides and going through a numerical optimization, the function for the back calculation of the values of the reference peptide retention times from the empirically measured values to the values in the indexed retention time scale, the parameters of the back calculation function for this particular experimental run are determined. Using these parameters which are specific for the particular experimental run, a prediction is made for the retention time of the target peptides.

This prediction can then be used for the identification of the target peptide or a multitude of target peptides, for the determination of retention time windows for the analysis of target peptides, as a score in case there are differences between the predicted and the experimentally determined retention time, or as a tool for selecting slices of data when MRM and/or SWATH techniques are used.

In contrast to in silico prediction such as SSRCalc, iRTa values can be determined many times and stored in a database or similar together with the identity of the analyte. In order to be more accurate in predicting retention time one can use the set of iRTa values for one specific analyte to determine an average iRTa, median iRTa or the like. The values can also be stored with reference to chromatography specific parameters such as a specific mobile phase composition, mobile phase pH, stationary phase and temperature.

As mentioned above, according to a first preferred embodiment in step f) a linear regression function is used as the transformation function and in step g) the optimized parameters of this linear regression are used for the calculation of the predicted empirical retention time value (RTp).

According to another preferred embodiment in step c) a linear regression function is used as the transformation function and for the calculation of iRTa the optimized parameters of this transformation function are used.

The set of reference peptides preferably comprises a multitude of reference peptides, so for example at least 3, at least 4, or at least 5 reference peptides, most preferably in the range of 5-15 reference peptides which, under the analytical conditions used in step e) cover and in a well distributed manner sample the retention time window of essentially all peptides of interest. In the case of SWATH, the set of reference peptides can also be optimized for the precursor m/z range that will be used in the SWATH method. If the whole precursor m/z range for SWATH is split into several precursor m/z ranges and measured in separate runs, than a multitude of reference peptide sets can be employed, each optimized for a certain precursor m/z range. The expression set of reference peptides shall also, according to one embodiment, include peptide like polymers which cover an appropriate and preferably large m/z range.

In step b) and/or in step e) an LC tandem mass spectrometry method are preferably used, preferably LC-MRM or LC-SWATH.

The predicted empirical retention time value (RTp) according to a first aspect of the invention is used for the identification of the corresponding target peptide and/or for the determination of a retention time window for the corresponding target peptide and/or to define one or more regions where the target peptide cannot occur.

The predicted empirical retention time value (RTp) according to a further aspect of the invention is used for the identification of the corresponding target peptide, and the retention time difference between the predicted empirical retention time value (RTp) and the effectively measured empirical retention time value, is used as a score for the validation of the target peptide identification. The set of retention time differences of confidently identified peptides (e.g. the reference peptides) can be used to determine the general distribution of those differences which can again be used to scale a score based on retention time differences.

The predicted empirical retention time value (RTp) according to yet another aspect of the invention is used for the identification of the corresponding target peptide, and the effectively measured empirical retention time value (RTe) of a target peptide is back calculated into a corresponding indexed retention time value in the next retention time scale using the numerically adapted transformation function determined in step f), and the difference between this value of the indexed retention time and of the corresponding associated indexed retention time value (iRTa) is used as a score for the validation of the target peptide identification.

In step b) and/or in step e) LC-MRM or LC-SWATH can be used, and the predicted empirical retention time value (RTp) can be used for corresponding selective data analysis of data slices characterizing the target peptide.

The predicted empirical retention time value (RTp) according to yet another aspect of the invention can be used to define regions where the target peptide cannot occur. These regions can be used in a statistical sense to empirically approximate expected signals under the assumption of the null hypothesis (compare to decoys) (Reiter, Rinner et al. 2011). The null hypothesis corresponds to the case where the targeted peptide cannot be detected. Ultimately, signals representing an accurate approximation of the null hypothesis are used to derive a confidence for the target peptide signals by means of a false discovery rate. In other words those regions can be used to determine the complexity of the sample which allows to calculate the likelihood that a signal as good (or better) than an observed one occurs by chance without effectively detecting the target peptide.

According to yet another preferred embodiment of the invention, in step b) and/or in step e) LC-MRM or LC-SWATH is used in scheduled mode, and wherein the predicted empirical retention time value (RTp) is used to adjust during the run the RT-window position and RT-window size of to be eluted analytes based on statistics of already eluted analytes.

An important element for high reliability measurements using the method according to the invention is the provision of an optimized set of reference peptides which, so to speak, sufficiently sample the retention time range usually available for complex samples in proteomics. One highly optimized such set has been developed in the context of the present invention. According to yet another preferred embodiment therefore, the at least two reference peptides are used selected from the group consisting of the sequences SEQID01-SEQID11, or variants thereof with essentially the same chromatographic behaviour (iRT) and in which not more than two amino acids, preferably not more than one amino acid are replaced by another amino acid and/or added terminally at the C- and/or the N-terminus. Preferably this set does not only comprise 2 such reference peptides, but preferably at least 5, or at least 9, most preferably the full set of 11 reference peptides as defined above. Most preferably this set of 11 peptides with exactly the sequences as defined in SEQID01-SEQID11 is used.

Furthermore, the present invention relates to a computer program product for use in the general context of the above-mentioned method. Preferably this computer program product is on or comprises a tangible computer-readable storage medium (e.g. CD, DVD, solid-state disk, data disk) whose contents include a program with instructions being executed on a processor so as to control a device for chemical analysis. According to a first aspect the corresponding computer program product is tailored to be used for carrying out and controlling a method as outlined above.

According to a second aspect of the computer program product this product controls at least the steps of f) translating empirical retention time values (RTe) of reference peptides measured with LC-MS on a second complex sample into an indexed retention time scale by numerically adapting the transformation function for the conversion of the retention time values (RTe) into indexed retention time values such that the calculated indexed retention time values (iRTe) calculated based on the measured retention time values (RTe) of the reference peptides optimally match the assigned indexed retention time values (iRTr), and g) determining the predicted empirical retention time value (RTp) of the at least one further peptide by using the numerically adapted transformation function determined in step f).

In relation with the computer program product all the particulars of the method as outlined above can be implemented, so the above mentioned embodiments in relation with the method equivalently apply to and shall be understood as to be disclosed also in connection with the computer program product.

The computer program can also have access to and be interactively linked to a database or similar with pre-determined iRTa for a large number of peptides. The values can also be stored with reference to one or more chromatography specific parameters such as a specific mobile phase composition, mobile phase pH, stationary phase and/or temperature or a combination thereof. The database can also store several iRTa values for a single peptide in order to derive an expected variance of iRTe which can be used for several aspects of the invention. Such aspects are for instance choosing the appropriate size of the scheduling window for LC-MRM. Another aspect is determining regions outside of the window where the peptide cannot appear. Another aspect is deriving a score from the difference between iRTa/RTp and iRTe/RTe, where the difference can be modified according to the expected variance of iRTe/RTe. Another aspect is choosing the appropriate size of the RT-window for slicing out data parts in LC-SWATH. Yet another aspect is choosing the appropriate window size when RTp is adjusted during the run.

As already outlined above, the present invention also relates to a set of reference peptides which is specifically adapted and suitable for use in a method as outlined above. Correspondingly therefore the present invention also pertains to a set of reference peptides for use in a method as outlined above, e.g. in the form of a ready to use solution comprising at least this set of reference peptides in a corresponding suitable solvent, normally water. Said set comprises at least 5 preferably at least 9, most preferably 11 peptides selected from the group consisting of SEQID01-SEQID11, or variants thereof with essentially the same (individual) retention behaviour (iRT) and in which not more than two amino acids, preferably not more than one amino acid are replaced by another amino acid and/or added terminally at the C- and/or the N-terminus.

Essentially the same individual retention behaviour means that if not exactly the peptide according to the defined sequences is used, the corresponding modification of the sequence by replacement of not more than 2 different amino acids within one peptides or the addition of not more than 2 further amino acids terminally (meaning in case of additional amino acids not more than one at each end), the correspondingly modified peptide still has essentially the same iRT value. Typically within the total spread of iRT in a scaling as e.g. outlined below in formula (1) the difference to the original is smaller than 5, preferably smaller than 2.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Definitions

Figure 1:
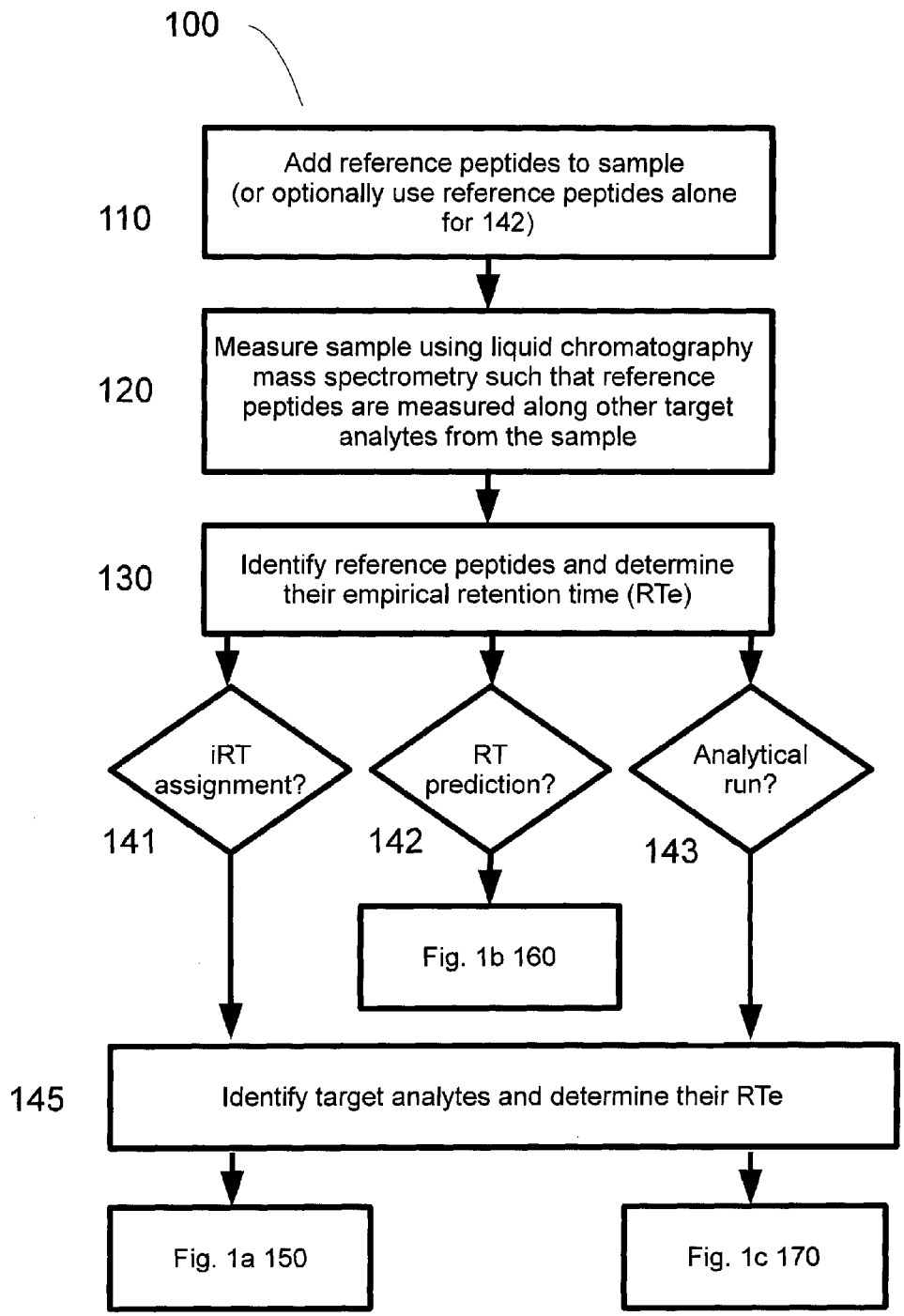
FIG. 1 is a flow diagram that describes iRT assignment, RT prediction and iRT validation and defines the terms iRTa, iRTe, RTp, and RTe, wherein in FIG. 1a the assignment of iRT values (iRTa) based on reference peptides is described, in FIG. 1b the determination of the predicted retention time (RTp) is given, in FIG. 1c the determination of empirical iRT values (iRTe) is given.

Target analyte/peptide: defines the analyte that is to be detected, quantified or generally analyzed. In the case of MRM, for each target analyte, transitions are defined and programmed into the mass spectrometer prior to the LC-MS run. In the context of LC-SWATH and other detection methods coupled to LC the target analyte is the analyte that is searched, detected, quantified or more generally analyzed post run by means of analysis of the data that can also contain signals from more than the anticipated targets.

Precursor ion/peptides: tryptic peptides or other protein cleavage products that are generated by protein cleavage for instance using proteases. The peptides are optionally chromatographically separated. Prior to analysis in the mass spectrometer the precursors are ionized typically to produce positively charged, protonated forms of the precursors.

LC-SWATH: refers to data independent acquisition methods where the precursor window is widened, and analytes from many precursor ions at the same time are fragmented. Specific reference is made to patent applications EP 10 009595.9 and U.S. 61/383,137 and the corresponding published subsequent applications claiming priority thereof, the content of which is included into the specification as concerns this technique.

Retention time: refers to the point in a chromatographic profile where the analyte shows its maximal intensity (apex).

Reference peptides/analytes: are peptides or generally analytes that are known to be present in a sample. They can be exogenous analytes that are added to the sample, known endogenous analytes or other known signals, e.g. from background contaminations.

Scheduled Acquisition: refers to mass spectrometric acquisition of data that is dependent on the retention time. Most commonly scheduled acquisition methods are used in LC-MRM experiments where transitions of target analytes are only measured around the time of the anticipated retention time. Moreover, acquisition can also be scheduled in LC-SWATH and generally LC-MS/MS.

Retention time window: In scheduled acquisition the retention time window (RT-window) defines the start and the end-time of acquisition for an analyte.

Some preferred uses of the proposed method as described below are directed toward protein-related analysis. Thus, for convenience the following description refers to proteins and related fragments, e.g. polypeptides that arise from enzymatic digestion. These polypeptides are ionized to form precursor ions and optionally are fragmented into product ions.

Although the description focuses on examples related to polypeptides, the scope of the description is not limited to the analysis of polypeptides. Persons having ordinary skills in chemical analysis will recognize that principles of the invention are applicable to analysis of other chemical compounds, such as small organic molecules, lipids, carbohydrates, other biopolymers like DNA, RNA, sugar-based biopolymers, mixed systems etc.

iRT as Relative Retention Time Scale:

Currently, two main approaches are used to predict the peptide retention times for a specific set up: (I) preliminary empirical measurement and (II) in silico prediction.

In the first approach (I), target peptides are first measured over the entire gradient under the conditions of the main experiment for the determination of the specific retention time.

The advantage of this direct approach is that it cancels out peptide-intrinsic variance (above factor (i)) and variance of the set up (above factor (ii) and to a certain extent also (iii)).

The disadvantage is that the resulting predictions are only valid for one specific experimental set up and need to be repeated every time a single parameter is changed. If a large number of targets are to be measured this method can require many sample injections to schedule a single experimental method. It also requires that the targets can be easily identified over the whole gradient.

These limitations restrict the direct approach to experiments with very few targets.

An alternative approach (II) tries to predict in silico the intrinsic peptide RT, usually based on the peptide sequence. This prediction is then translated into real RT by a linear fit to a single calibration run. The most widely used RT prediction algorithm is SSRCalc.

The advantages of the in silico approach are that it requires only a single calibration run with no prior detection of the targets, and it can be used for an unlimited number of peptides.

The limitation of this method is its considerable lack of accuracy. Even the most sophisticated algorithm cannot fully account for all relevant physicochemical properties based on the sequence alone. This lack of accuracy forces the use of wide RT-windows in order to avoid missing or only partially capturing the elution of the peptide during acquisition.

The iRT instead allows for highly accurate prediction of RTs in LC-MS experiments. FIG. 1 shows a flow diagram that describes how measured retention times can be transformed into a dimensionless stable value, which we call indexed retention time (iRT) and used for identification of analytes.

a) Determination of an iRT Scale:

Physical reference peptides define an iRT standard. Preferably synthetic peptides with the sequence SEQID01-SEQID11 are used or any other set of peptides that elute in a range wide enough to cover early and late eluting analytes. In principle therefore also different sets of peptides can constitute the same iRT scale, including endogenous peptides or contaminants (such as keratin or trypsin) as long as they can be consistently observed across samples.

Figure 2:
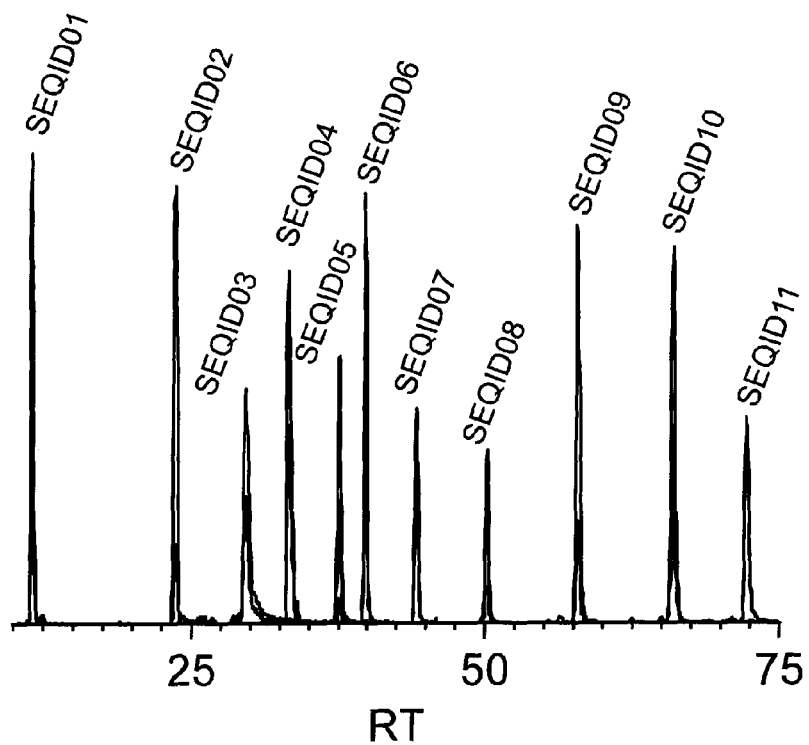
FIG. 2 depicts a measurement of 11 reference peptides that were designed such that they elute over a broad range when using reverse phase liquid chromatography for separation.

A concrete example how an iRT scale can be defined is given below:

We selected 11 peptides (SEQID01-SEQID11), tested them thoroughly for stability and wide range of elution and approximately equal spacing of RT and recorded a data-set with LC-MRM and C18-derivatized resin as column material, which we refer to as iRT-C18 scale (FIG. 2, Table 1).

Table 1 shows the 11 peptides with SEQID01-SEQID11 and their corresponding iRTr determined in an LC-MRM run using a linear chromatographic gradient.

| Sequence | Name | iRTr |
|---|---|---|
| LGGNEQVTR | SEQID01 | −24.92 |
| GAGSSEPVTGLDAK | SEQID02 | 0.00* |
| VEATFGVDESNAK | SEQID03 | 12.39 |
| YILAGVENSK | SEQID04 | 19.79 |
| TPVISGGPYEYR | SEQID05 | 28.71 |
| TPVITGAPYEYR | SEQID06 | 33.38 |
| DGLDAASYYAPVR | SEQID07 | 42.26 |
| ADVTPADFSEWSK | SEQID08 | 54.62 |
| GTFIIDPGGVIR | SEQID09 | 70.52 |
| GTFIIDPAAVIR | SEQID10 | 87.23 |
| LFLQFGAQGSPFLK | SEQID11 | 100.00* |

Retention times for all peptides were extracted, and then we artificially assigned the value 0 and 100 to the SEQID02 and SEQID11 respectively.

Given this assignment, the formula for the assignment of an iRTr (reference iRT values) value to a reference peptide x member of the 11 reference peptides on a chromatographic system with a linear gradient is:

$$iRTr = [(RT_x - RT_{SEQID02})/(RT_{SEQID11} - RT_{SEQID02})] * factor \quad (1)$$

where factor was chosen to be 100 but could be any number. The results are fixed iRTr values for the 11 reference peptides given in Table 1, each reference peptide is associated a iRTr, value. We assigned SEQID02 with the iRTr value of 0 because very early eluting peptides generally have higher variance in retention time and hence choosing SEQID02 is more robust. This approach can be applied to any set of at least two peptides to define an iRT scale. In this case a linear gradient was used to define the scale. For other types of gradients the same method can be used to define an iRT scale.

iRT scales defined for a specific set of peptides can be transformed into any other scale by means of relating the retention times of the two reference sets measured under the same conditions.

This can be done by translating the empirical retention time values (RTe) of the first set of reference peptides into the indexed retention time scale by numerically adapting the transformation function for the conversion of the RTe into indexed retention time values such that the indexed retention time values (iRTe) calculated based on the RTe of the first set of reference peptides closely/optimally match the assigned indexed retention time values (iRTr) of the first set of reference peptides. The RTe of the second set of reference peptides can then be converted into the indexed retention time scale using the same conversion function. The iRTr of the second set of reference peptides can then be used as the iRTr of the first set of reference retention time peptides.

b) Use of an iRT:

The method of using such an iRT scale for a real experiment with analytes is illustrated in FIG. 1. The scheme 100 requires the measurement of reference peptides (preferably more than two reference peptides), for which an iRT scale has already been established (see above a)), optionally together with the target analytes in step 110. Addition of reference peptides in 110 is accomplished ideally in a way such that the intensity of the signals of the same peptides will be sufficient to identify them without uncertainty.

Reference peptides and optionally the target analytes are measured in an LC-MS experiment in 120, preferably in an unscheduled LC-MRM experiment preferably using a linear gradient.

In 130 the reference peptides are identified and their retention time is determined. We refer to the retention time measured in an experiment as empirical retention time or RTe.

Determination of RTe for the reference peptides requires the unambiguous identification of the reference peptides. Any described method to extract and assign signals from MS data can be used as well as the iRT concept itself. Identification of reference peptides could also be done without acquisition of MS-data, for instance with LC-UV, as long as the signals can be identified unambiguously. Preferably the exact apex of the elution is identified. Preferably only unambiguous identifications are considered if more than 2 reference peptides are used to avoid inaccurate predictions in later steps.

After the extraction of RTe values of the reference peptides in 130 further steps are dependent on the task of the experiment.

Figure 1A:
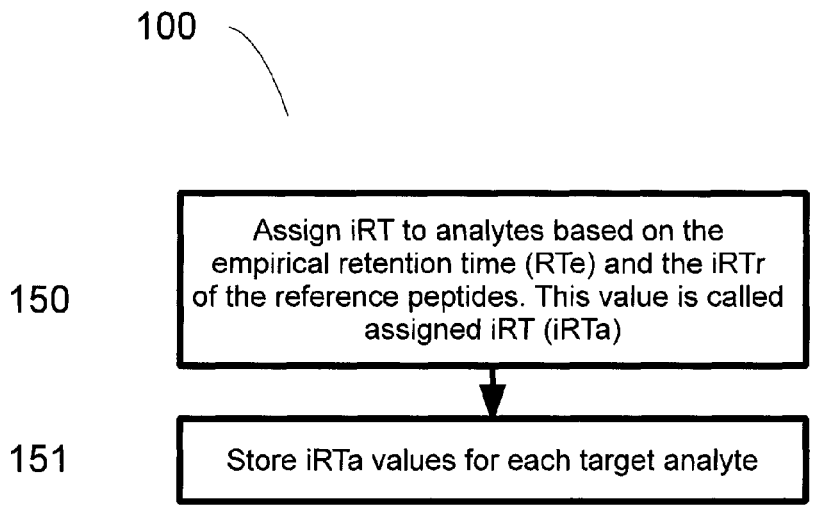
Figure 1B:
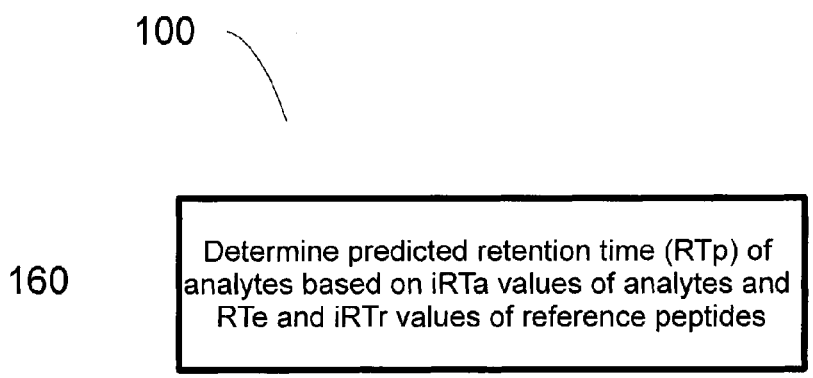

If for instance the target analytes have no iRT value assigned yet (target analytes not measured yet), it is required to determine this iRT value in an iRT assignment step 141 as illustrated in FIG. 1a (see also description of a) above, left branch in FIG. 1) method 150. If the task is to predict retention times of target peptides in 142 method 160 as illustrated in FIG. 1b is used (central branch in FIG. 1).

Figure 1C:
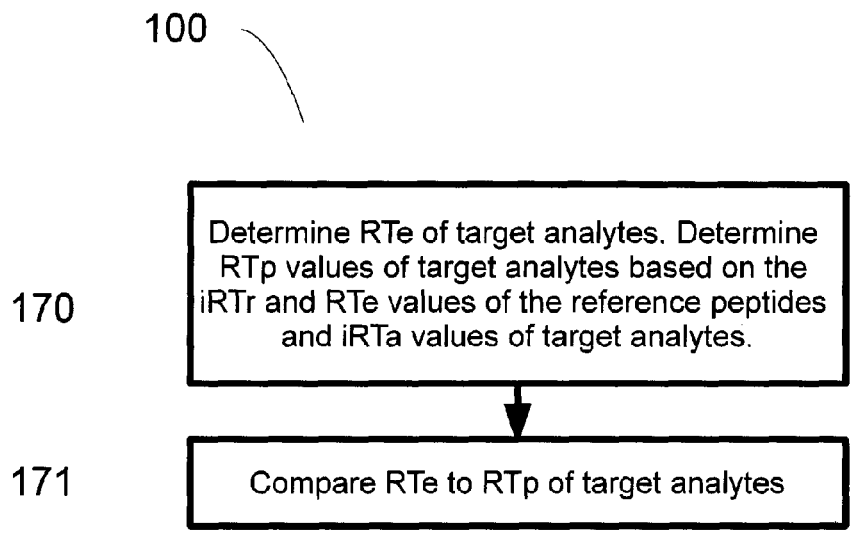

If the task is an analytical task, e.g. to identify or quantify target peptides in a LC-MS experiment in 143 method 170 as illustrated in FIG. 1c is used (right branch in FIG. 1).

c) Determination of iRTa Values of Target Analytes in a Run:

The formula, as described in 150, to assign an iRT value (141) as given in FIG. 1a for a target peptide, so determining the corresponding iRTa value for each target peptide, using the RTe values of the target peptides (145) on a chromatographic system with a linear gradient is:

$$iRTa = f(RTe) = m*RTe + n \quad (2),$$

where m is the slope and n is the y-intercept from the linear regression of the iRTr values by the measured RTe values of the reference peptides (130) of this specific experiment/run. The formula to derive m and n is:

$$iRTr = f(RTe) = m*RTe + n \quad (3)$$

So for each run a linear regression on the reference peptides is carried out independently and this linear regression for this run is then used for conversion of the measured RTe values of the analytes into iRTa values, thereby removing inter-run differences.

In order to minimize residual variance of retention time (intra-run differences) the measurement can also be repeated and average iRTa used as final iRTa values. Also, the iRTa could be refined in later stages using reliable data derived as described here.

Any RTe determined for a target analyte in 145 can be converted into iRTa by formula (2) and the iRTa can be stored for further use (151), e.g. with a computer program.

If the chromatographic system is set up with a different type of gradient, when compared to the gradient chosen for establishing the iRT scale, then the fit has to be chosen accordingly, e.g. the fit can be approximated with a number of linear fits in between neighboring reference peptides.

If identification of reference peptides is difficult, robust linear regression can also be applied in order to reduce the influence of outlier data points resulting from rare erroneous reference peptide identifications.

Figure 3:
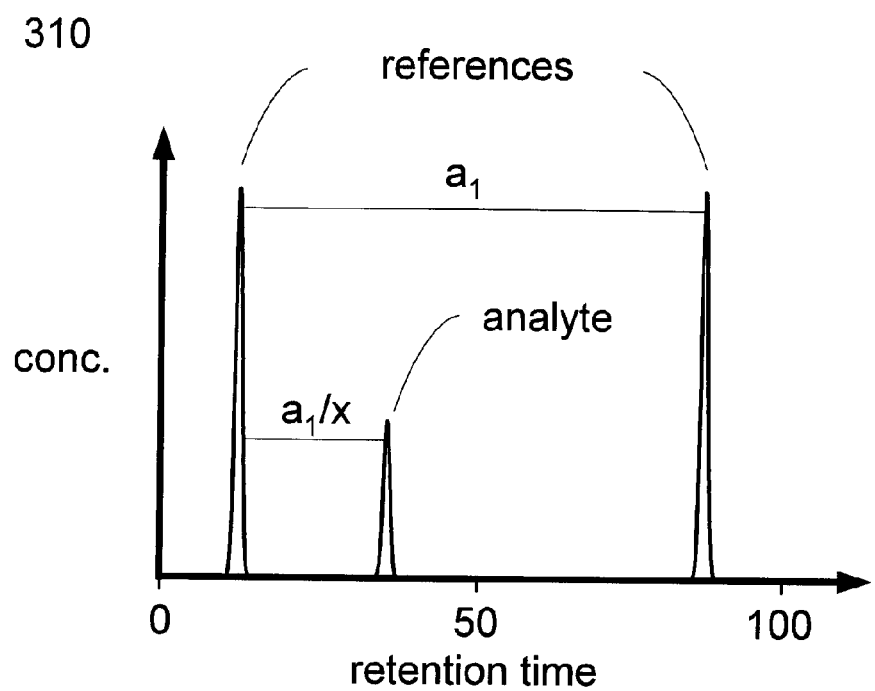
FIG. 3 is a schematic illustration of the stability of iRT of an analyte relative to the retention times of two reference peptides when using different linear chromatographic gradients.
Figure 3:
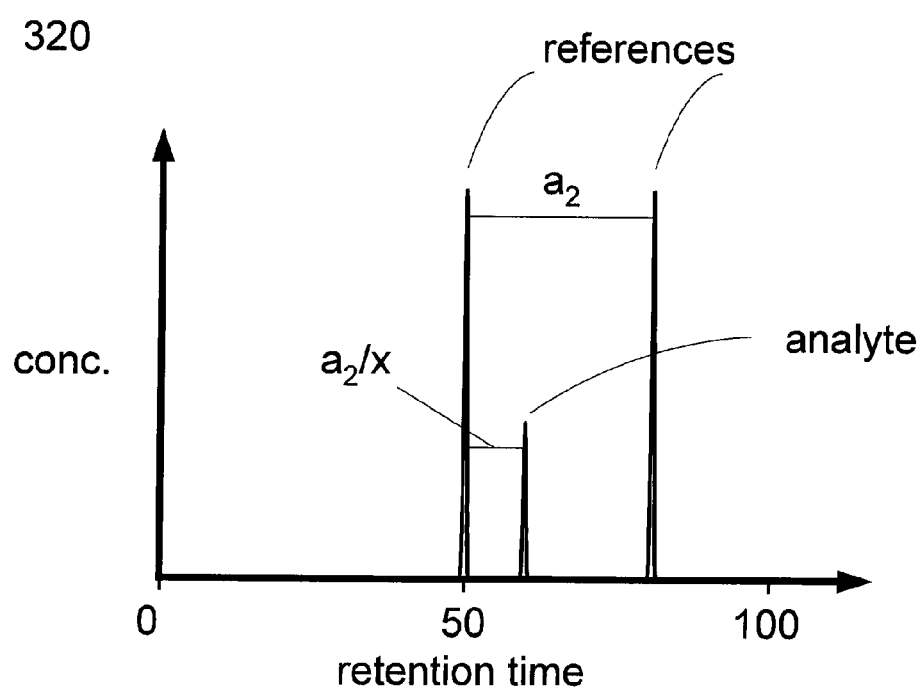

FIG. 3 illustrates that the iRTa are independent of the LC-system setup as indicated with the constant factor x describing the relative position of the target analyte to the reference peptides. Two different LC setups are depicted in 310 and 320 respectively.

d) Prediction of RTp Values of Target Analytes:

The formula (160) to predict a retention time value (142) as given in FIG. 1b for a target peptide, so determining the corresponding RTp value for each target peptide, using the iRTa values of the target peptides (150) on a chromatographic system with a linear gradient is:

$$RTp = f(iRTa) = m*iRTa + n \quad (4),$$

where m is the slope and n is the y-intercept from the linear regression of RTe values of the reference peptides from 130 of this specific experiment/LC-run by the iRTr. The formula to derive m and n is:

$$RTe = f(iRTr) = m*iRTr + n \quad (5)$$

If the chromatographic system is set up with a different type of gradient, when compared to the gradient chosen for establishing the iRT scale, then the fit has to be chosen accordingly, e.g. the fit can be approximated with a number of linear fits in between neighboring reference peptides.

If identification of reference peptides is difficult, robust linear regression can also be applied in order to reduce the influence of outlier data points resulting from erroneous reference peptide identifications.

Figure 4:
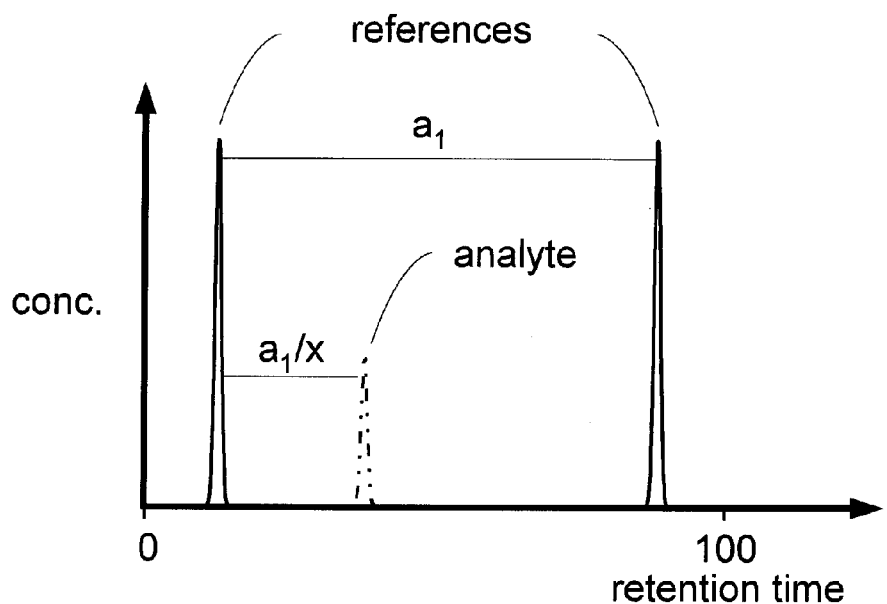
FIG. 4 is a schematic illustration of the different uses of RTp. RTp can either be used for prediction of retention time of future LC runs or for analysis of the actual LC run from which the RTp was derived.
Figure 4:
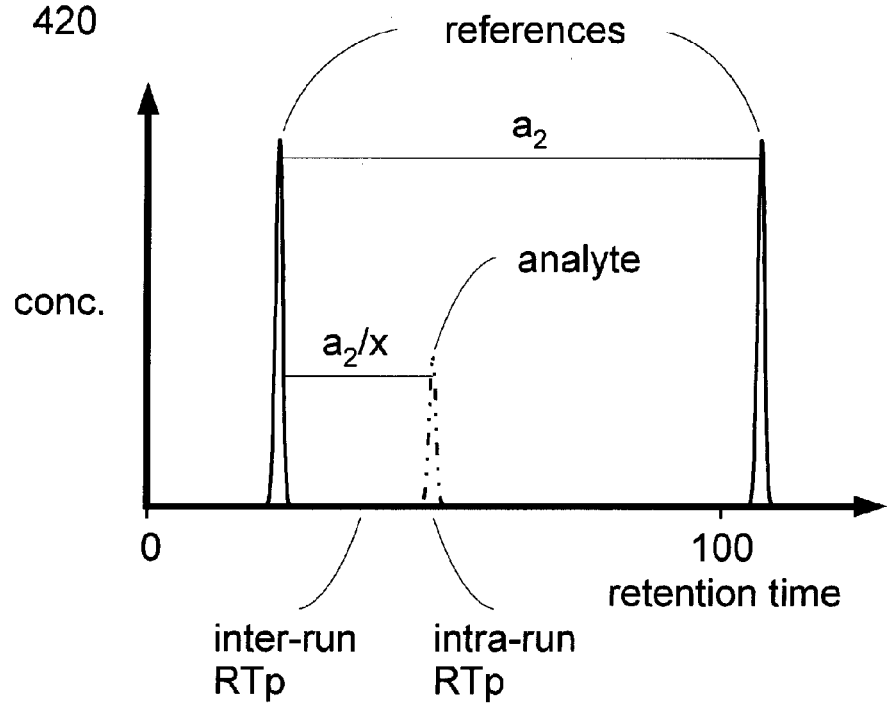

From FIG. 4 it becomes clear that this method allows predicting retention times on various LC-system setups with formula (4). Two reference peptides are shown exemplarily. FIG. 4 also illustrates that RTp values can either be used to predict the expected retention time for a target analyte within the same run where the reference peptides were measured (intra-run prediction, 420) or for any consecutive future run (inter-run prediction, 410 applied to 420). Intra-run prediction is generally more accurate than inter-run prediction. In the case of inter-run prediction the target analytes do not necessarily have to be in the sample, only the reference peptides do.

Figure 5:
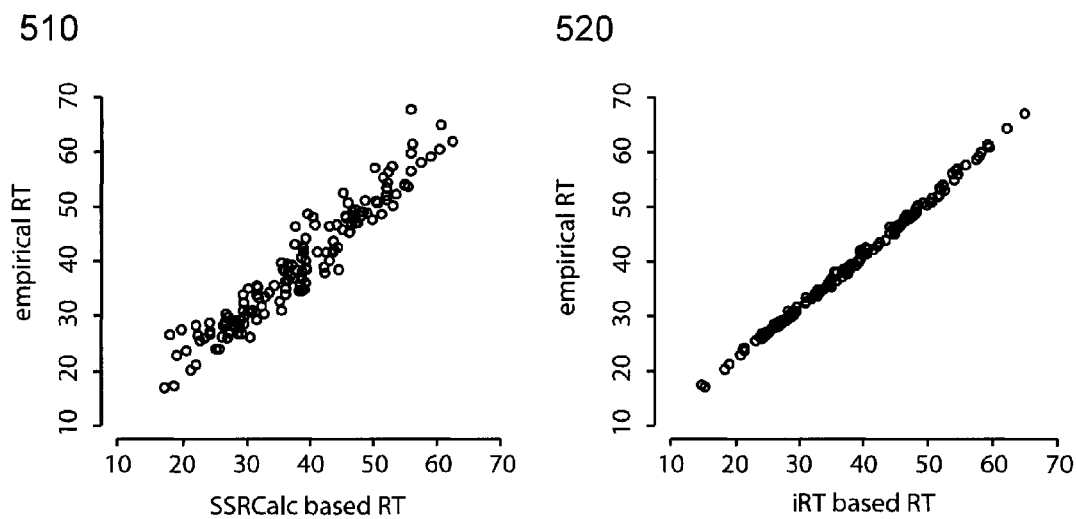
FIG. 5 shows the improvement of retention time prediction when comparing iRT to in silky) prediction using SSRCalc.

We found that the iRT method shown in 510 allows for 5 times smaller RT scheduling windows than RTs predicted using SSRCalc shown in 520, offering a substantial increase in measurement throughput as well as analytical precision (FIG. 5).

e) Analytical Run:

In 143 an analytical run is described where target analytes are measured together with reference peptides as described in 100 ff. Preferably, the RTp values of the analytes are known and have been derived in 160 from iRTa values of the target analytes. The RTe values of the reference peptides are derived in 130. RTp values can be derived using formula (4) above.

Then RTe values can be determined for the target analytes (170). In contrast to d) the target analyte needs to be present in the sample. The potential RTe can then be compared to the predicted value RTp.

Alternatively, in order to be independent of the LC gradient used, RTp and RTe of the target analyte can also be converted into the iRT scale. If so, RTp corresponds to iRTa and the empirical iRT (iRTe) can be determined analogously to iRTa using formula (2). These iRTe values of the target analytes are based on the actual chromatographic conditions and the actual RTe values of the target analytes.

In other words, first linear regression is used to relate the iRTr values to measured RTe values of the reference peptides of this specific experiment/run from 130 to calculate m and n in formula (2) for this run, where m is the slope and n is the y-intercept from the linear regression of iRTr by RTe of the reference peptides for this run as given in formula (3).

Again, if identification of reference peptides is difficult robust, linear regression can also be applied in order to reduce the influence of outlier data points resulting from erroneous reference peptide identifications.

Then iRTe values of the analytes are calculated by RTe of the target analytes using these values for m and n as determined in the linear regression of formula (3) and then using them as given in above formula (2) for the calculation of the iRTe values of the target analytes:

$$iRTe = f(RTe) = m*RTe + n \quad (6)$$

Figure 6:
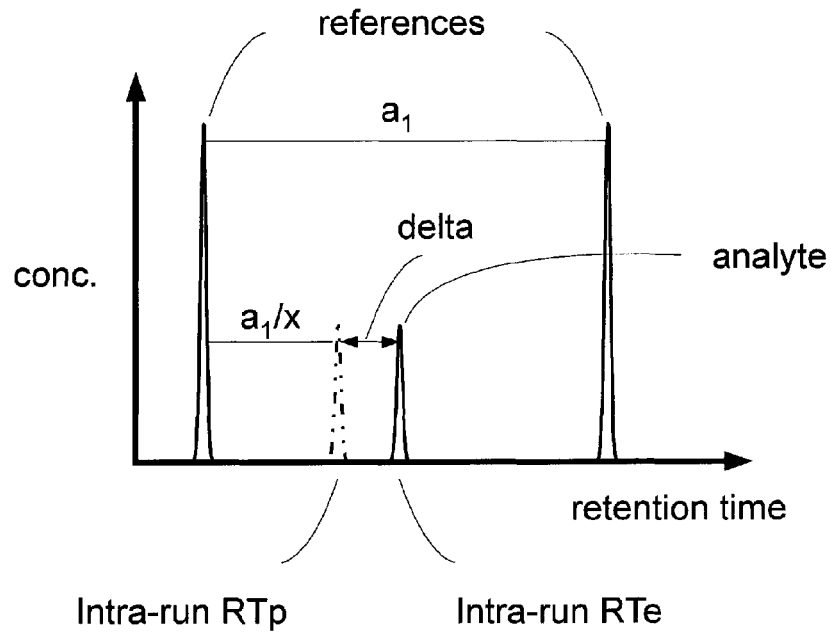
FIG. 6 schematically depicts the occurrence of residual intra-run fluctuations that result in deviations from the intra-run predicted retention time.

In the case of a perfect linearity the difference between iRTa and iRTe of a target analyte should be 0, even in cases where a shift in the LC system would occur. There might for instance be fluctuations in parts of the gradient, which violate the assumption of perfect linearity. This variance we call residual variance and it results in an absolute value of delta-iRT|iRTa−iRTe|>0 (171). FIG. 6 illustrates this as a deviation of the expected ratio a1/x from the RTe.

Use of Delta iRT as a Score:

The difference of the iRTa and empirical iRT (iRTe) constitutes a value that can serve as score or sub-score for the validation of identification for instance in an LC-MRM or LC-SWATH experiment or generally for any detector coupled to a LC system such as LC-UV. The invention of using the delta-iRT (|iRTa−iRTe|) is that LC-variance described above is thereby cancelled out and the separation power of that score increases. FIG. 6 and method 143 describe how a delta-iRT score can be derived as a difference between iRTa and iRTe or RTp and RTe respectively. The delta value in iRT scale has the advantage of being independent of the underlying LC system. Using delta-iRT or delta-RT scale however, has no influence on the power of the score for identification. Preferably the absolute difference is used as a score. The smaller the score is, the higher the correspondence of predicted and measured RT.

Figure 7:
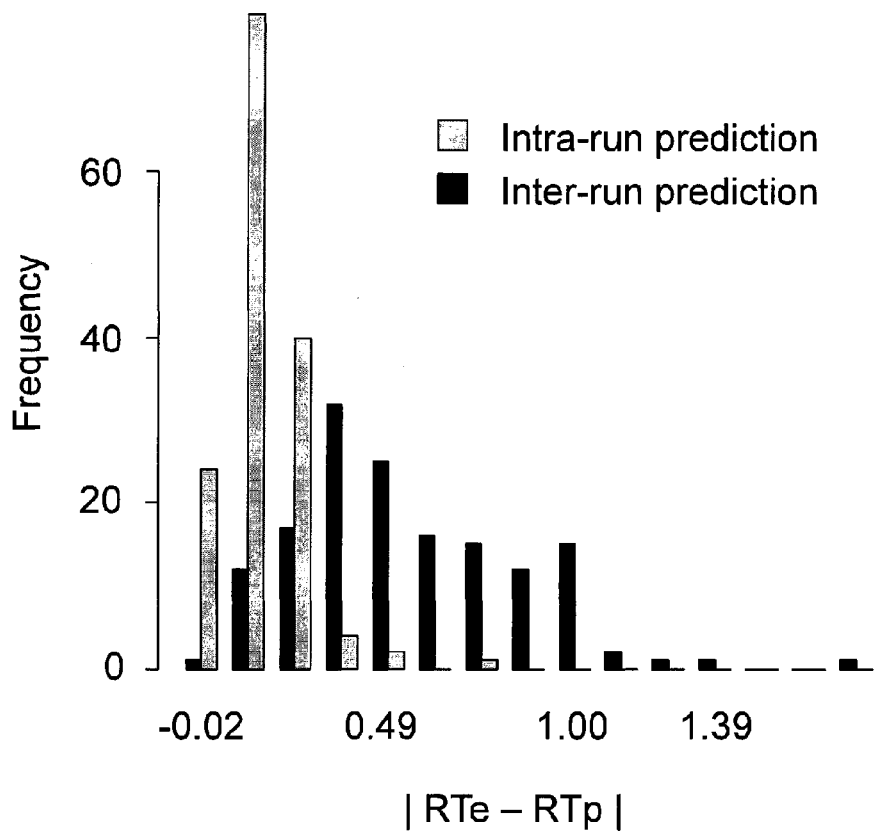
FIG. 7 depicts an exemplary comparison of two different types of delta retention time using data of a measurement of 160 target peptides; retention time prediction for future LC runs is compared to retention time prediction within an LC run.

FIG. 7 shows a comparison based on LC-MRM of the delta score based on inter-run predicted RTp (derived from an earlier run) to intra-run predicted RTp (derived from within the same run). As can be seen from this empirical data when based on the intra-run prediction this score is stronger as exemplified by the smaller variance. This, even though the data was generated using exactly the same LC system and the runs were performed right after each other. The delta value can generally be expressed in RT space or iRT space. In order to make inter-run and intra-run prediction better comparable in FIG. 7 the RT space was used.

Examples of Use of this Score

Use of iRTe to Slice LC-SWATH and LC-MRM Data:

In LC-MRM, data acquisition for the target analyte transitions is necessarily longer than the elution of the actual peak. This is especially the case if the acquisition is non-scheduled. Without knowing the expected signal RT the identification of the true signal is complicated by the presence of noise and generally interfering signals. In SWATH-MS the acquisition is commonly not scheduled and consequently this problem is aggravated by the huge complexity of the data that contains multiple convoluted fragment spectra in each scan.

By determining the RT scale for each specific experiment based on the aforementioned addition of reference peptides into the sample and using the iRTr and RTe of the reference peptides and the target analyte iRTa in each experiment for the conversion in the RT scale (determination of m and n for each experiment), we describe here how the data can be preprocessed in a way that only slices of the data are extracted and analyzed for the presence of the target analyte. This RT-slicing effectively increases the specificity of data analysis by reducing the amount of data that is searched for the presence of the target signal. Further, it also reduces the amount of data that needs to be processed which in turn increases the computation performance. The method is preferably applied to LC-MRM and LC-SWATH, where the biggest gain in specificity is expected for LC-SWATH data.

Figure 8:
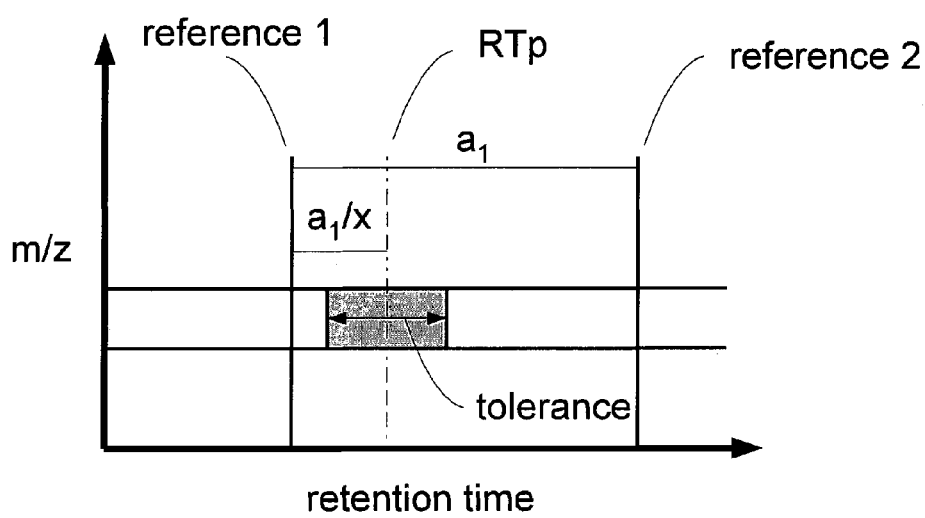
FIG. 8 schematically illustrates how the intra-run predicted retention time together with the expected m/z of an analyte can be used to extract only the relevant part of a data set for analysis after the measurement.

FIG. 8 illustrates the process. A specific data range that is expected to contain the target analyte fragment ions is selected based on the calculated precursor m/z and the precursor selection window. Based on method 100 the intra-run predicted RT (RTp) is determined for the target analyte based on the reference peptide information (determination of m and n) and on the target analyte iRTa. As the target analyte is expected to elute close to the intra-run predicted RTp a narrow window is defined based on the expected accuracy (tolerance) of the intra-run predicted RTp such that the target analyte is within this window with very high probability. Only acquired data within that window is then searched for the presence of the signal of the target analyte. The window size can be chosen based on previous experience. More advanced, the window size can also be determined based on the distribution of delta RTp−RTe values of highly confident identifications. The highly confident identifications can be derived from the reference analytes and/or from a first pass analysis of the data set. The window size can then be chosen larger than twice the maximal absolute delta RTp−RTe value of the highly confident identifications. Another possibility is to choose the window size such that the chance of missing an analyte is smaller than x, e.g. 0.001. The probability can be estimated based on the delta RTp−RTe values of highly confident identifications.

Figure 9:
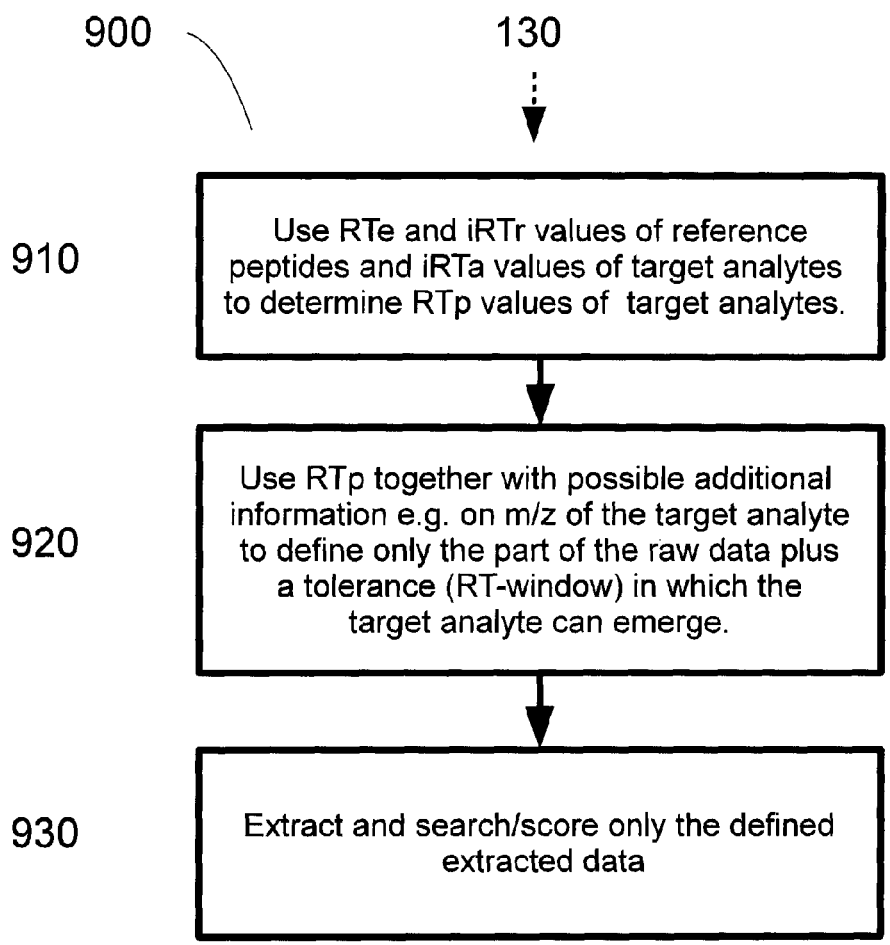
FIG. 9 is a flow diagram describing the working steps involved when using the intra-run predicted retention time for extraction of the relevant data from the data set.

FIG. 9 is a flow diagram of method 900. The method 900 is based on method 100. The acquisition of data 120 is done in LC-MS mode or preferably in LC-SWATH mode. Reference peptides are identified in 130. The iRTr values and RTe values of the reference peptides of that specific LC-MS run are used for the determination of m and n in a linear regression similar to formula (5) using method 910. Targets to be analyzed are selected. Their precursor m/z is determined and their iRTa is converted into RTp in method 910 using the previously determined m and n and formula (4). iRTa values can be stored in a database or the like and accessed e.g. by a computer program that performs the method. In 920 a swath for LC-SWATH analysis or more generally an m/z range is selected based on the m/z of the precursor and optionally also based on the m/z of the fragment ion. In 920 also, a narrow window around RTp that is expected to contain the target analyte is selected (RT-window). In 930 a slice of the raw data, corresponding to the previously determined m/z range and RT-window, is extracted (see above for how the RT-window can be determined). By effectively ignoring large parts of the data within the m/z range, the specificity is increased and the computational requirement is reduced.

Addition of reference peptides in 110 is accomplished ideally in a way that the intensity of the signals of the same peptides is sufficient to identify them without uncertainty. Preferably peptides with the sequence SEQID01-SEQID11 are used or another set of peptides that elute in the range from the earliest eluting analytes of interest to the latest eluting analytes. Alternatively to 110 a set of endogenous peptides or proteins that can be identified with high confidence can be used if they are translated into an iRT scale according to method 100.

In 120 the sample is measured in LC-MS mode, separating the peptides chromatographically and ionizing them by any suitable ionization process such as electrospray ionization or MALDI. During that process ions are further fragmented to produce fragment ions. The reference peptides thereby undergo the same procedure; preferably they were mixed with the sample in 110. Acquisition of the data can either happen in MRM mode, isolating a specified m/z window around the target precursor ion (Q1) and the target fragment (Q3) whereby transitions for the reference peptides are measured in addition to the target analytes. Or acquisition can happen in SWATH mode or any other mode where full fragment ion spectra are recorded with a high time resolution. Any restriction in time range and/or precursor m/z range and/or fragment ion m/z range can be used. Also segments of time and/or segments of precursor m/z and/or segments of fragment ion m/z can be used. Even combinations of non-adjacent segments of precursor m/z can be used if some intermediate storage of ions before fragmentation is possible. This combination of non-adjacent segments can be used to prevent interferences of pairs of isotopically light and heavy labeled peptides when e.g. two channel labeling of protein samples is used. In cases where the whole m/z range is measured over the full elution time the reference peptides are naturally measured together with the other analytes. In cases where only parts of the m/z range and/or parts of the elution time data is acquired care must be taken that the corresponding reference peptides are included or tailor made sets of reference peptides have to be used. Also peptide-like polymers can be used as reference analytes if they show an even and fine grained mass distribution over a large m/z range.

In 130 the RTe of the reference peptides are determined. Preferably this happens in a first pass of the data with any appropriate analysis method. In the case of MRM, transitions from the reference peptides are analyzed first. Care must be taken that the identification of these peptides can be made with high confidence because calculation of the intra-run expected retention times is based on this scale. The extracted RTe values are preferably compared to a standard scale of the same peptides to verify the expected relationship, e.g. a linear correlation between measured and standard set.

Again, if identification of reference peptides is difficult, robust linear regression can also be applied in order to reduce the influence of outlier data points resulting from erroneous reference peptide identifications.

In 910 the empirical retention time of the reference peptides determined in 130 is used to translate the iRTa of the target analytes into RTp as described in method 100. One or more target analytes are selected and their RTp is determined preferably from a catalog that contains the iRTa determined in previous experiments by method 100. The availability of such a catalog for all conceivable targets will increase the applicability of this method.

An RT-window of interest is defined based on the intra-run predicted RTp of the target analyte. The width of that window is determined such that it contains the target analyte with high confidence. Preferably it is determined based on the delta-RT (|RTe−RTp|) of the reference peptides next to the target analyte (reference 1 and reference 2 in FIG. 8) to capture local run-specific effects such as deviations from perfect gradient linearity. Alternatively, the window size can be determined based on other statistics, such as prior observations of target delta-iRT/delta-RT or based on data from a first pass of parts of the data without applying steps 910 and 920. In general, the smaller the chosen RT-window is, the greater the gain in specificity. However, by making the RT-window too small one risks to miss the target analyte.

In 930 parts of the data within the m/z range (of precursor and/or optionally fragment ion) and the RT-window are selected for data analysis. For SWATH data this is preferably done on the level of raw data. Here the data volumes are very large and by selecting a small slice of the data a significant reduction of data processing can be achieved. In MRM data volumes are commonly smaller and the slicing of the data can happen on the raw data or on the data analysis step. In any case, signal identification, scoring and quantification happen only in the data slice within the RT-window.

Use of RTp to define retention time regions where target analyte will not appear:

The predicted empirical retention time value (RTp) can also be used to define regions where the target peptide cannot occur. These regions can be used in a statistical sense to empirically approximate expected signals under the assumption of the null hypothesis (compare to decoys) (Reiter, Rinner et al. 2011). The null hypothesis corresponds to the case where the target peptide cannot be detected. Ultimately, signals representing an accurate approximation of the null hypothesis are used to derive a confidence for the target peptide signals by means of a false discovery rate.

How to specify the RT-window where the target analyte is expected is described in detail in the preceding chapter. The RT-windows where the target analyte is not expected correspond to the complete RT range where target analytes are expected, exclusive of the RT-window where the target analyte is expected.

For MRM data, this specification of regions where the target analyte is not expected allows to achieve the same as with the explicit measurement of decoy transitions (non-sense transitions or negative controls) (Reiter, Rinner et al. 2011), with the advantage that it saves the measurement time of the decoy transitions and simplifies MRM experiment design.

Figure 10:
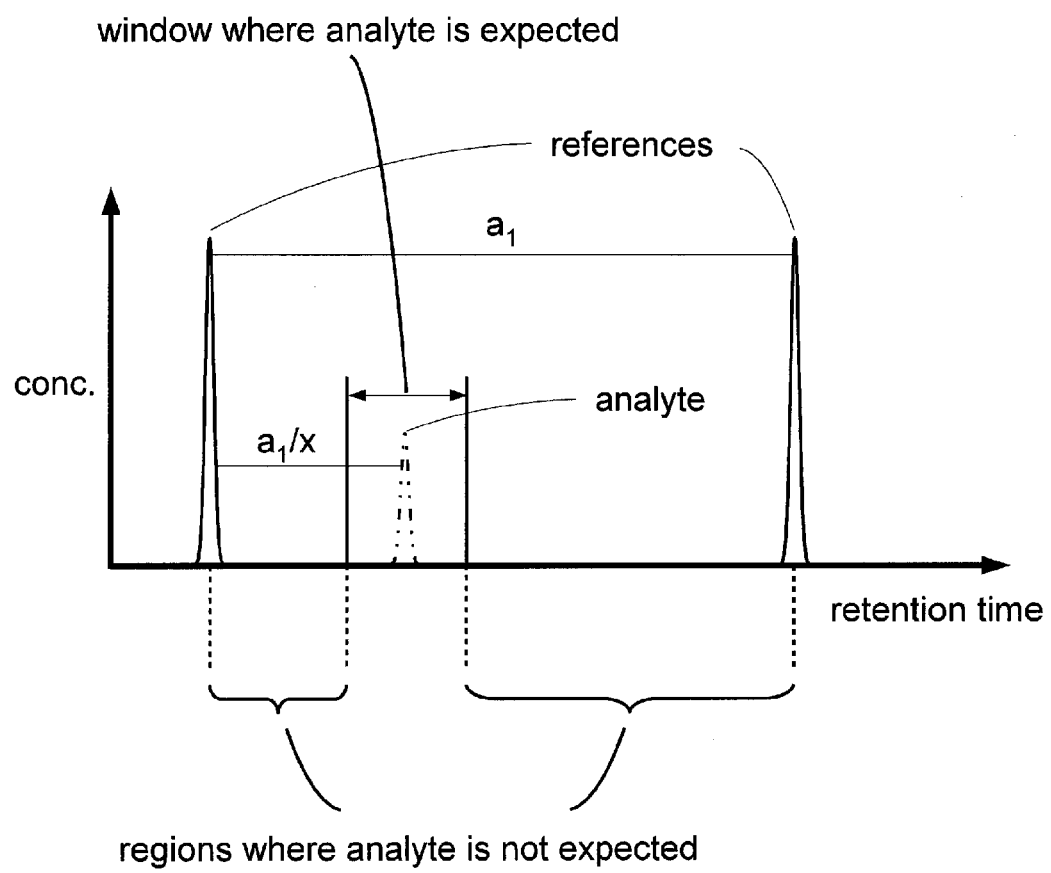
FIG. 10 shows how the RTp can be used to define regions where the analyte is not expected to occur. These regions can be used for statistical analysis of randomly occurring signals and ultimately for confidence estimation of target analyte signals.

In FIG. 10 the regions where the target analyte is not expected is illustrated by two flanking regions of the RT-window where the target analyte is expected. The regions should be chosen such that they do not correspond e.g. to regions where no target analyte is expected in general (for instance regions where the LC column is washed).

Dynamic Adjustment of Window Size for Scheduled MRM:

Method 900 describes the use of iRT to reduce the size of the RT-window post-run to improve data analysis. Essentially, the same method can be used to adjust the RT-window during the run (on the fly calibration) preferably in LC-MRM experiments or generally in all LC-MS applications where the acquisition is scheduled, i.e. the acquisition of a specific target analyte or a target m/z range happens only in defined RT-windows. Thereby, the dwell time for each target or target range can be minimized while at the same time the chance of missing a target due to variance in RTe is reduced.

As the reference peptides elute, the RTe values of the reference peptides are determined during acquisition (130). Initially, the adaption of RTp of the target analytes is done based on at least 2 reference peptides using formula (5) to determine m and n and formula (4) to determine RTp and preferably recalculated as more reference peptides elute.

One example for such and adjustment is:
1. Analytes or the reference peptides alone are identified as they elute from the column. Any method to identify analytes can be employed here as long as the analysis time is short enough to allow on the fly-calibration. Preferably only signals that are identified with high certainty are used to calculate the transformation function to convert iRTa into RTp using formula (4).
2. The RTp of the target analytes is calculated using the transformation function and the center of the RT-windows for the remaining analytes are chosen according to the new RTp (RTp normally being used as the center).
3. The window size is chosen based on available data of delta-RT (RTe–RTp) and or delta-RT of the current LC run. The tolerance is defined in a way that the remaining analytes are with a very high likelihood within the RT-window. Any other statistics that provides an expected elution time and an estimation of the maximally expected difference between RTe and RTp of the target peptide can be used here. Preferably, the delta-RT scores are calculated locally, i.e. the current deviation is weighted higher than deviations in the past (resp. at the beginning of the run). Thereby local fluctuations can be captured.
4. It is preferable to set up the measurement schedule in a way that initial window sizes are large enough to capture the analytes with high certainty before the effect of the recalibration sets in.

LIST OF REFERENCE SIGNS

| | |
|---|---|
| RT | retention time |
| RTe | empirical retention time, retention time measured in an experiment |
| iRT | indexed retention time |
| iRTa | assigned indexed retention time |
| RTp | predicted retention time |
| iRTe | empirical indexed retention time |
| $a_1, a_2, \ldots$ | retention time difference between two reference peaks |

LIST OF REFERENCE SIGNS -continued

| | |
|---|---|
| x | stable factor that determines the relative position of a target analyte when compared to two references |
| LC | liquid chromatography |
| MS | mass spectrometry |
| MRM | multiple reaction monitoring |
| m/z | mass divided by molecule charge |
| SRM | selected reaction monitoring |
| iRTr | reference iRT for reference peptide |
| $iRTr_x$ | iRTr for reference peptide x |
| 100 | iRT, RTe, iRTa, RTp and iRTe determination scheme |
| 110 | measurement of reference peptides optionally together with the target analytes |
| 120 | LC-MS experiment |
| 130 | identification of reference peptides and determination of their retention time |
| 141 | iRT assignment step |
| 142 | prediction of retention times of target peptides |
| 143 | analytical task |
| 145 | identification of analytes and determination of their retention time |
| 150 | determination of iRTa values of analytes |
| 151 | storage of iRTa values |
| 160 | prediction of RTp values of analytes |
| 170 | determination of iRTe values of the analytes |
| 171 | Compare RTe to RTp |
| 310 | exemplary LC setup and relation of analyte RT to reference RT |
| 320 | exemplary LC setup different to 310 and relation of analyte RT to reference RT |
| 410 | exemplary LC setup with RTp prediction |
| 420 | exemplary LC setup with RTp prediction and predicted RTp from 410 with similar LC setup |
| 510 | prediction of RT based on SSRCalc and comparison to RTe |
| 520 | prediction of RT based on iRT concept and comparison to RTe |
| 900 | slice extraction from LC-SWATH and LC-MRM using RTp |
| 910 | prediction of RTp values of analytes |
| 920 | slice extraction from LC-SWATH or LC-MRM based on RTp and an RT-window |
| 930 | Extract and search/score only the extracted slices from 920 |

The invention claimed is:

1. A method of chemical analysis, comprising;
   a) providing a first complex sample comprising a set of at least two reference peptides associated to an indexed retention time scale, as well as at least one further peptide,
   b) performing LC-MS on said complex sample and determining empirical retention time values RTe of the reference peptides and of the at least one further peptide,
   c) translating said empirical retention time values RTe of the reference peptides and of the at least one further peptide into the indexed retention time scale and associating to each reference peptide a reference indexed retention time value iRTr and to the at least one further peptide an associated indexed retention time value iRTa,
   d) providing a second complex sample comprising at least one polypeptide as well as said set of the at least two reference peptides,
   e) performing LC-MS on said second complex sample and determining empirical retention time values RTe of the reference peptides,
   f) translating the empirical retention time values RTe of the reference peptides into the indexed retention time scale by numerically adapting the transformation function f $$RTe = f(iRTr)$$

for the conversion of the retention time values RTe into indexed retention time values such that the calculated indexed retention time values RTe calculated based on the measured retention time values RTe of the reference peptides optimally match the assigned indexed retention time values (iRTr) of the reference peptides, g) determining the predicted empirical retention time value RTp of the at least one further peptide by using the numerically adapted transformation function f determined in step f) as follows:

RTp=f(iRTa)

wherein the predicted empirical retention time value (RTp) is used for at least one of the following: the identification of the corresponding further peptide; the determination of a retention time window for the corresponding further peptide; and, the definition of one or more regions where the further peptide cannot occur.

2. The method according to claim 1, wherein in step f) a linear regression function is used as the transformation function and wherein in step g) the optimized parameters of this linear regression are used for the calculation of the predicted empirical retention time value RTp.

3. The method according to claim 1, wherein in step c) the translation is carried out by numerically adapting the transformation function f iRTr=f(RTe)

for the conversion of the indexed retention time values iRTr into the empirical retention time values RTe of the reference peptides, wherein as the transformation function a linear regression function is used and wherein for the calculation of iRTa the optimized parameters of this transformation function f are used.

4. The method according to claim 1, wherein the set of reference peptides comprises at least 3 reference peptides which, under the analytical conditions used in step e) cover and in a well distributed manner sample the retention time window of essentially all peptides of interest.

5. The method according to claim 1, wherein in step b) and/or in step e) an LC tandem mass spectroscopy method is used.

6. The method according to claim 1, wherein in step b) and/or in step e) an LC tandem mass spectroscopy selected from the group of LC-MRM or LC-SWATH is used.

7. The method according to claim 1, wherein the predicted empirical retention time value RTp is used for the identification of the corresponding target peptide, and wherein the retention time difference between the predicted empirical retention time value RTp and the effectively measured empirical retention time value RTe, is used as a score for the validation of the target peptide identification.

8. The method according to claim 1, wherein the predicted empirical retention time value RTp is used for the identification of the corresponding target peptide, and the effectively measured empirical retention time value RTe of a target peptide is back calculated into a corresponding indexed retention time value in the next retention time scale using the numerically adapted transformation function f determined in step f), and the difference between this value of the indexed retention time and of the corresponding associated indexed retention time value iRTa is used as a score for the validation of the target peptide identification.

9. The method according to claim 1, wherein in step b) and/or in step e) LC-MRM or LC-SWATH is used, and wherein the predicted empirical retention time value RTp is used for corresponding selective data analysis of data slices characterizing the target peptide.

10. The method according to claim 1, wherein in step b) and/or in step e) LC-MRM or LC-SWATH is used in scheduled mode, and wherein the predicted empirical retention time value RTp is used to adjust during the run the RT-window position and RT-window size of to be eluted analytes based on statistics of already eluted analytes.

11. The method according to claim 1, wherein at least two reference peptides are selected from the group consisting of the sequences SEQID01-SEQID11, or variants thereof with essentially the same retention behaviour and in which not more than two amino acids are replaced by another amino acid or added terminally at the C-Terminus, the N-Terminus, or both C-Terminus and N-Terminus.

12. A non-transitory computer program product, whose contents include a non-transitory program with instructions being executed on the processor so as to control a device for chemical analysis using a method according to claim 1, or at least f) translating empirical retention time values RTe of reference peptides measured with LC-MS on a second complex sample into an indexed retention time scale by numerically adapting the transformation function for the conversion of the retention time values RTe into indexed retention time values such that the calculated indexed retention time values RTe calculated based on the measured retention time values RTe of the reference peptides optimally match the assigned indexed retention time values iRTr of the reference peptides, and g) determining the predicted empirical retention time value RTp of the at least one further peptide by using the numerically adapted transformation function f determined in step f).

13. Set of reference peptides for use in a method according to claim 1, said set comprising at least 5 peptides selected from the group consisting of SEQID01-SEQID11, or variants thereof with essentially the same retention behaviour and in which not more than two amino acids replaced by another amino acid or added terminally at the C-Terminus, the N-terminus, or both the C-Terminus and the N-terminus.

14. The method according to claim 1, wherein the set of reference peptides comprises at 4 reference peptides, which, under the analytical conditions used in step e) cover and in a well distributed manner sample the retention time window of essentially all peptides of interest.

15. The method according to claim 1, wherein the set of reference peptides comprises at least 5 reference peptides, which, under the analytical conditions used in step e) cover and in a well distributed manner sample the retention time window of essentially all peptides of interest.

16. The method according to claim 1, wherein the set of reference peptides comprises in the range of 5-15 reference peptides which, under the analytical conditions used in step e) cover and in a well distributed manner sample the retention time window of essentially all peptides of interest.

17. The method according to claim 1, wherein the predicted empirical retention time value (RTp) is used to define one or more regions where the target peptide cannot occur, in a statistical sense to empirically approximate expected signals under the assumption of a null hypothesis.

18. The method according to claim 1, wherein at least two reference peptides are selected from the group consisting of the sequences SEQID01-SEQID11, or variants thereof with essentially the same retention behaviour and in which not more than one amino acid is replaced by another amino acid or added terminally at the C-Terminus, the N-terminus, or both the C-Terminus and the N-terminus.

19. A non-transitory computer program product, on or comprising a tangible non-transitory computer-readable storage medium that is non-transient and whose contents include a program with instructions being executed on the processor so as to control a device for chemical analysis using a method according to claim 1, or at least f) translating empirical retention time values of reference peptides measured with LC-MS on a second complex sample into an indexed retention time scale by numerically adapting the transformation function for the conversion of the retention time values into indexed retention time values such that the calculated indexed retention time values iRTe calculated based on the measured retention time values RTe of the reference peptides optimally match the assigned indexed retention time values iRTr of the reference peptides, and g) determining the predicted empirical retention time value RTp of the at least one further peptide by using the numerically adapted transformation function f determined in step f).

20. A set of reference peptides for use in a method according to claim 1, said set comprising at least 9 peptides selected from the group consisting of SEQID01-SEQID11, or variants thereof with essentially the same retention behaviour and in which not more than two amino acids are replaced by another amino acid or added terminally at the C-Terminus, the N-terminus, or both the C-Terminus and the N-terminus.

21. A set of reference peptides for use in a method according to claim 1, said set comprising 11 peptides selected from the group consisting of SEQID01-SEQID11, or variants thereof with essentially the same retention behaviour and in which not more than two amino acids are replaced by another amino acid and/or added terminally at the C-Terminus, the N-terminus, or both the C-Terminus and the N-terminus.

22. A set of reference peptides for use in a method according to claim 1, said set comprising 11 peptides selected from the group consisting of SEQID01-SEQID11, or variants thereof with essentially the same retention behaviour and in which not more than one amino acid is replaced by another amino acid and/or added terminally at the C-Terminus, the N-terminus, or both the C-Terminus and the N-terminus.

* * * * *

SEQUENCE LISTING

<160> NUMBER OF SEQ ID NOS: 11

<210> SEQ ID NO 1
<211> LENGTH: 9
<212> TYPE: PRT
<213> ORGANISM: Artificial Sequence

```
<220> FEATURE:
<223> OTHER INFORMATION: Synthetic peptide

<400> SEQUENCE: 1

Leu Gly Gly Asn Glu Gln Val Thr Arg
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

<400> SEQUENCE: 2

Gly Ala Gly Ser Ser Glu Pro Val Thr Gly Leu Asp Ala Lys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide

<400> SEQUENCE: 3

Val Glu Ala Thr Phe Gly Val Asp Glu Ser Asn Ala Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide

<400> SEQUENCE: 4

Tyr Ile Leu Ala Gly Val Glu Asn Ser Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5

Thr Pro Val Ile Ser Gly Gly Pro Tyr Glu Tyr Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide

<400> SEQUENCE: 6

Thr Pro Val Ile Thr Gly Ala Pro Tyr Glu Tyr Arg
1               5                   10

<210> SEQ ID NO 7
<211> LENGTH: 13
<212> TYPE: PRT
<213> ORGANISM: Artificial Sequence
<220> FEATURE:
```

```
<223> OTHER INFORMATION: Synthetic peptide

<400> SEQUENCE: 7

Asp Gly Leu Asp Ala Ala Ser Tyr Tyr Ala Pro Val Arg
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic peptide

<400> SEQUENCE: 8

Ala Asp Val Thr Pro Ala Asp Phe Ser Glu Trp Ser Lys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide

<400> SEQUENCE: 9

Gly Thr Phe Ile Ile Asp Pro Gly Gly Val Ile Arg
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

Gly Thr Phe Ile Ile Asp Pro Ala Ala Val Ile Arg
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide

<400> SEQUENCE: 11

Leu Phe Leu Gln Phe Gly Ala Gln Gly Ser Pro Phe Leu Lys
1               5                   10
```